United States Patent [19]
Paradis

[11] Patent Number: 6,117,114
[45] Date of Patent: Sep. 12, 2000

[54] SWABBABLE NEEDLELESS VALVE ADAPTATIONS

[76] Inventor: Joseph R. Paradis, P.O. Box 22238, Hilton Hd., S.C. 29925

[21] Appl. No.: 09/074,257
[22] Filed: May 7, 1998
[51] Int. Cl.⁷ ................................................. A61M 5/00
[52] U.S. Cl. ........................ 604/246; 604/249; 604/533
[58] Field of Search .............................. 604/30, 33, 246, 604/249, 282–533, 534–537, 284, 905; 251/149.1

[56] References Cited

U.S. PATENT DOCUMENTS 5,676,346 10/1997 Leinsing ............................ 251/149.1

Primary Examiner—Wynn Wood Coggins
Attorney, Agent, or Firm—George E. Kersey, Esq.

[57] ABSTRACT

A valve adapted to actuators with various tolerances by having a flexible axial wall extend inwardly from an input of a housing containing a plurality of stationary and longitudinally extending ribs and by having the flexible axial wall surroundingly engage each inserted actuator, regardless of tolerance variations.

15 Claims, 13 Drawing Sheets

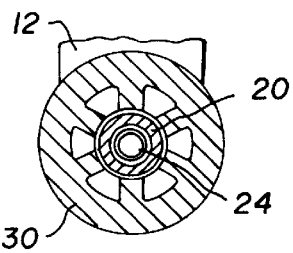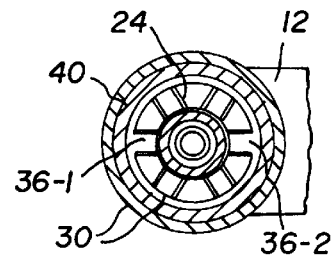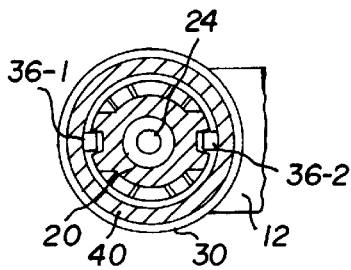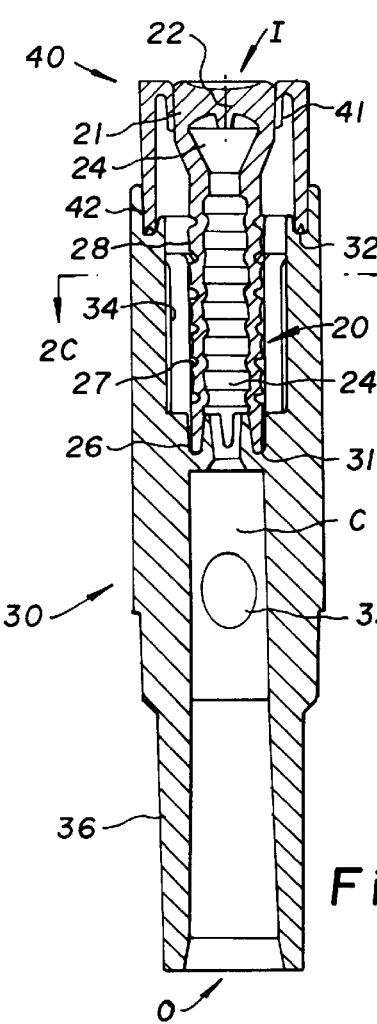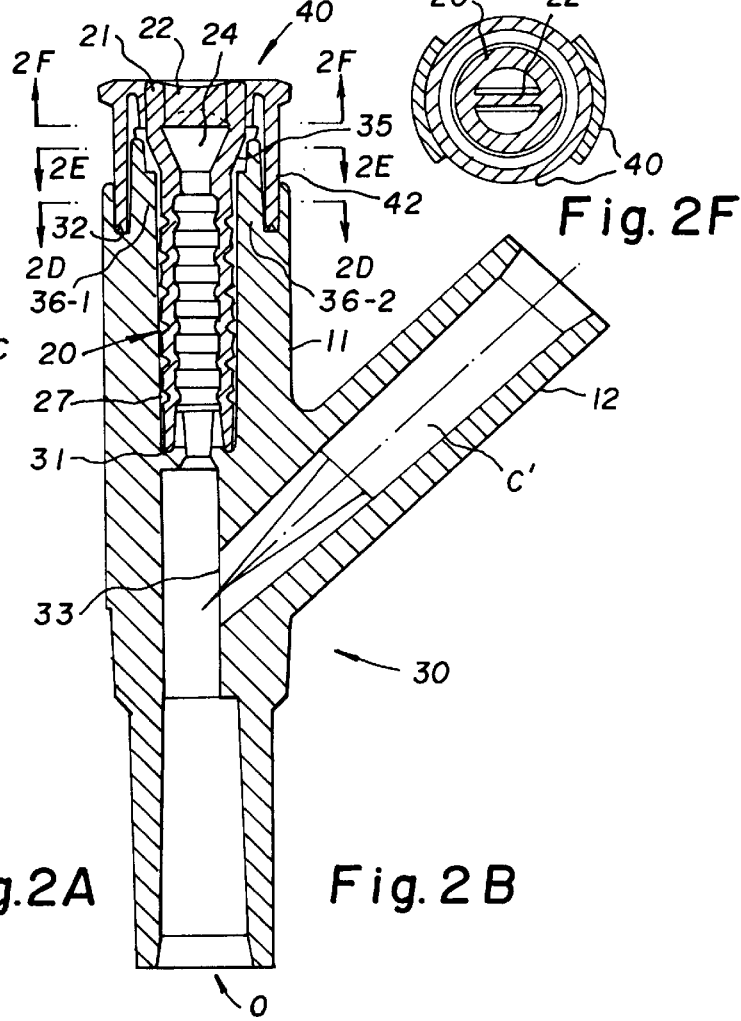

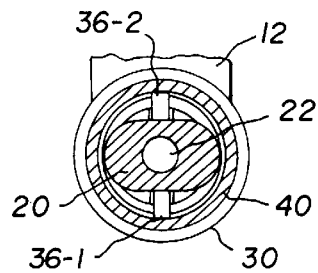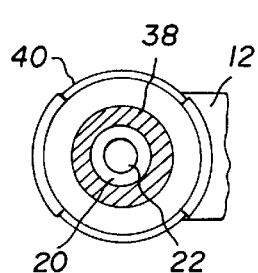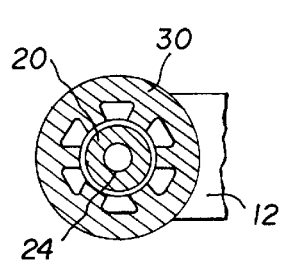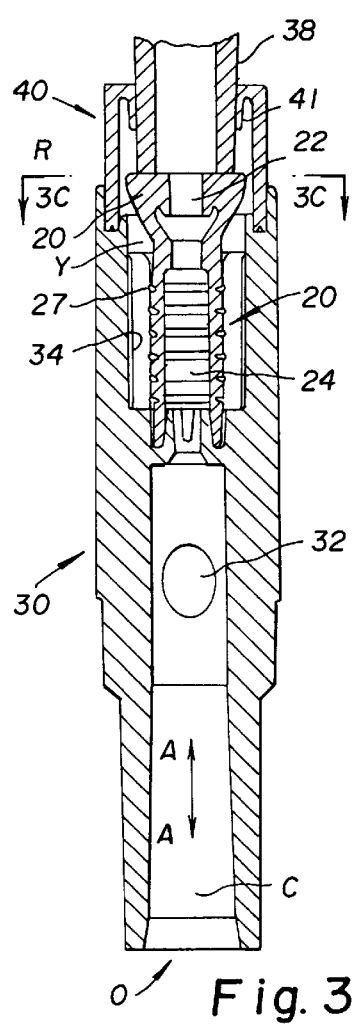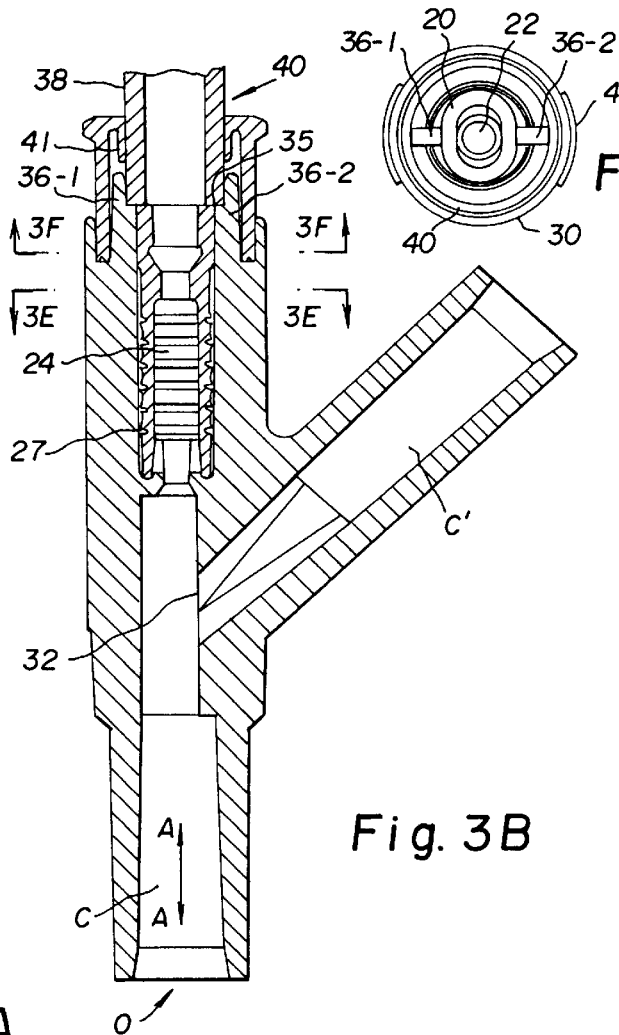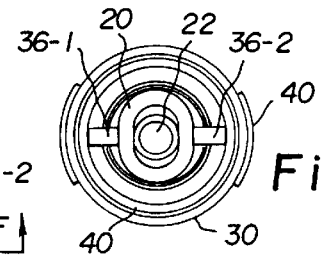

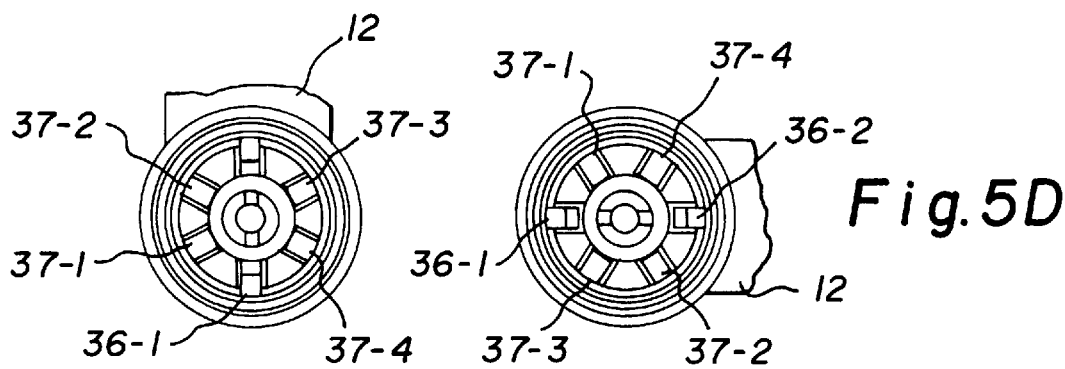
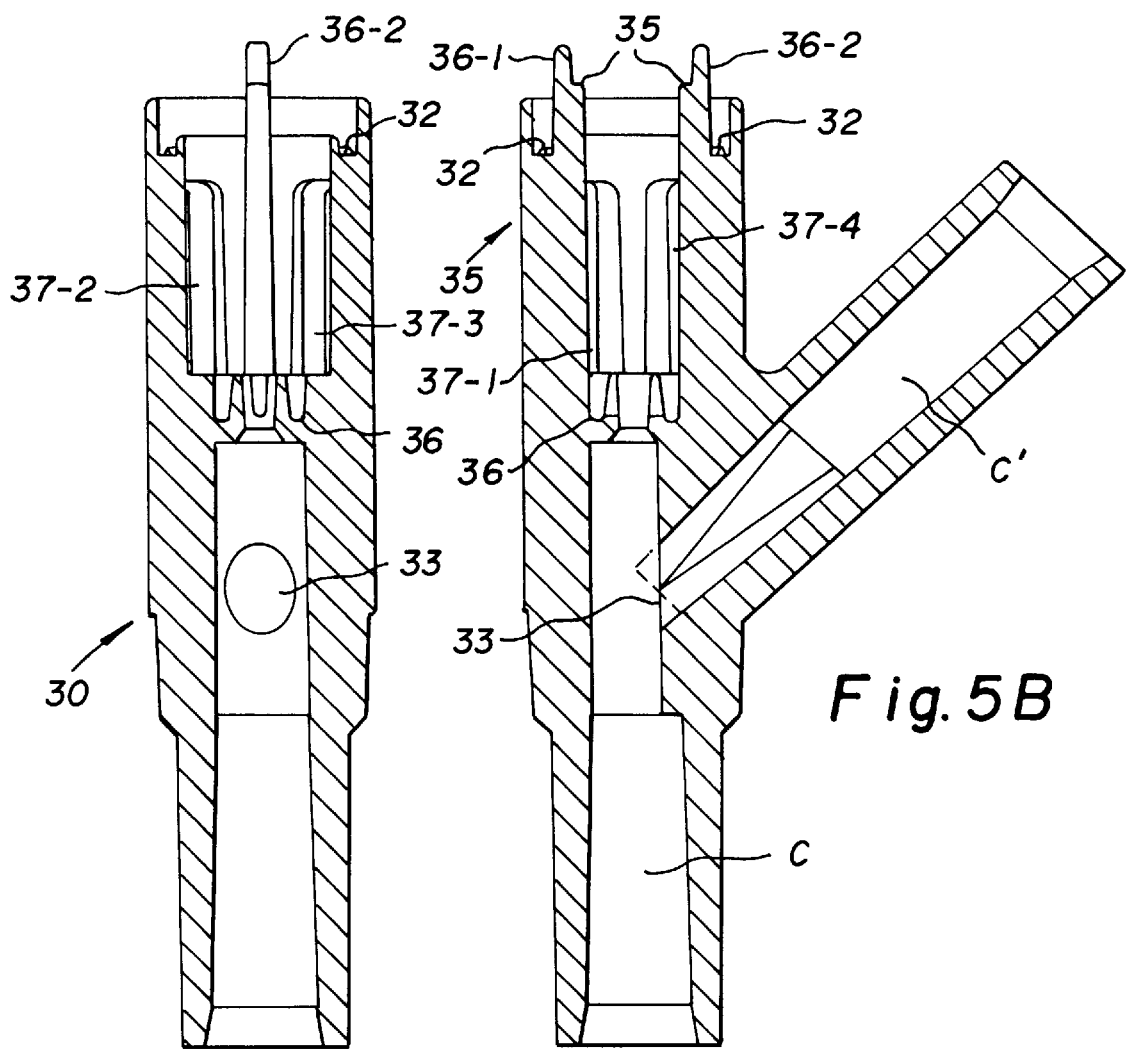

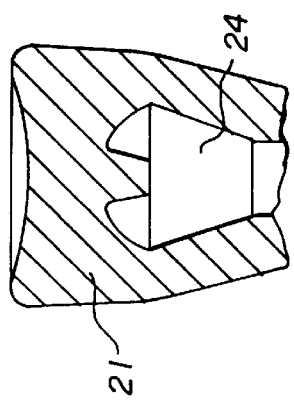
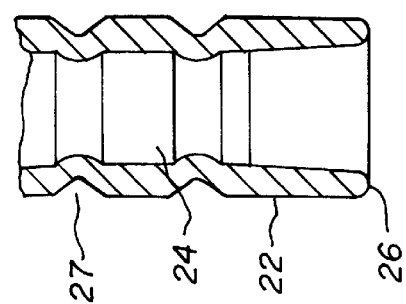
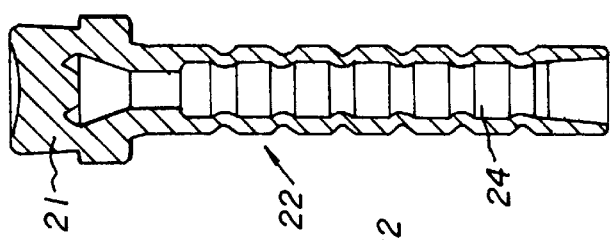
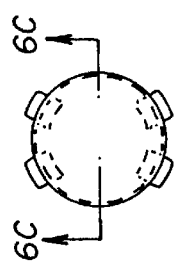
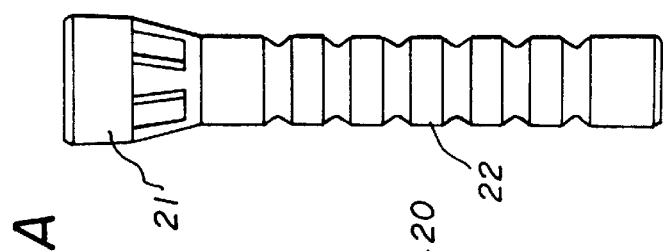
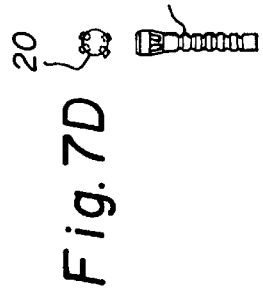

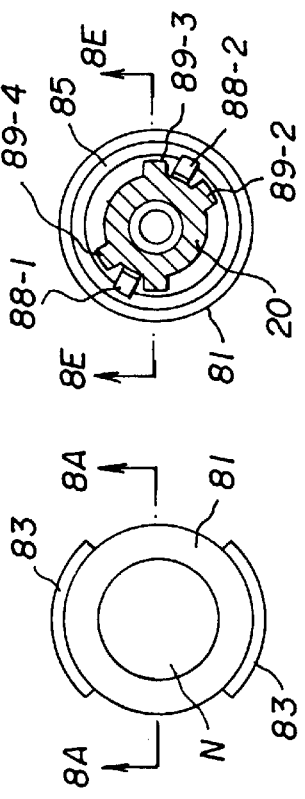
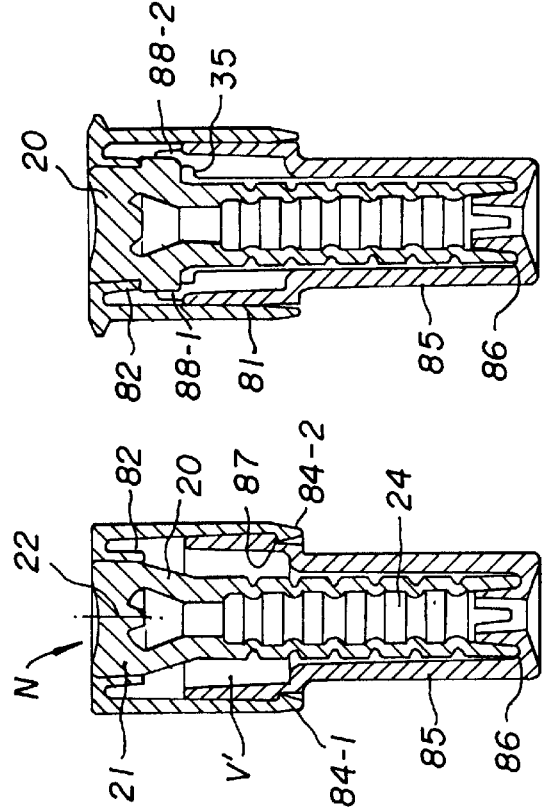

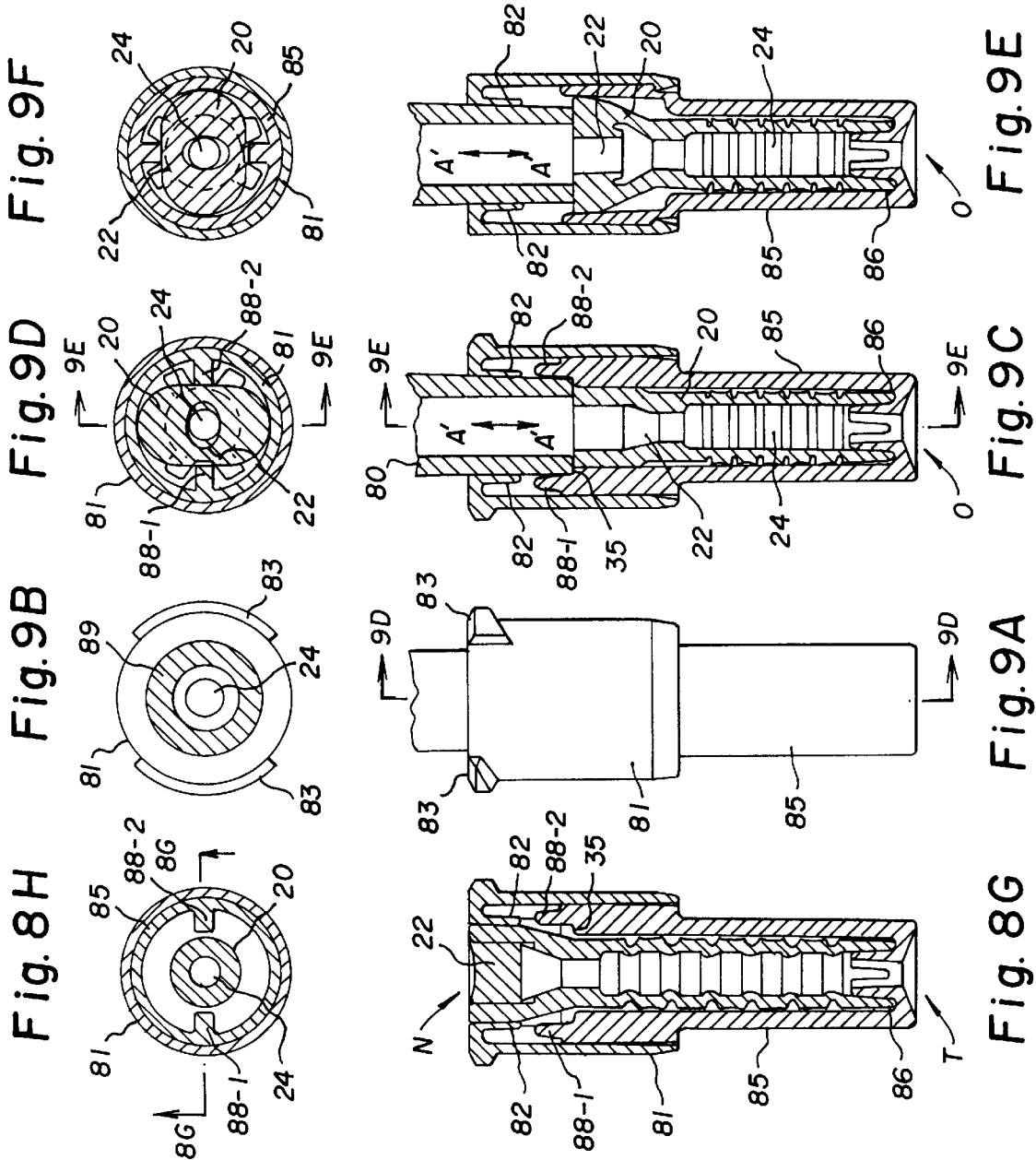

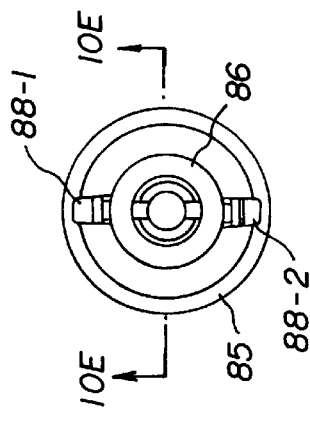
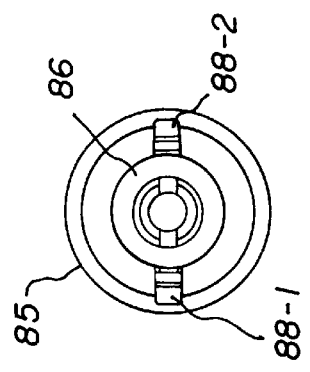
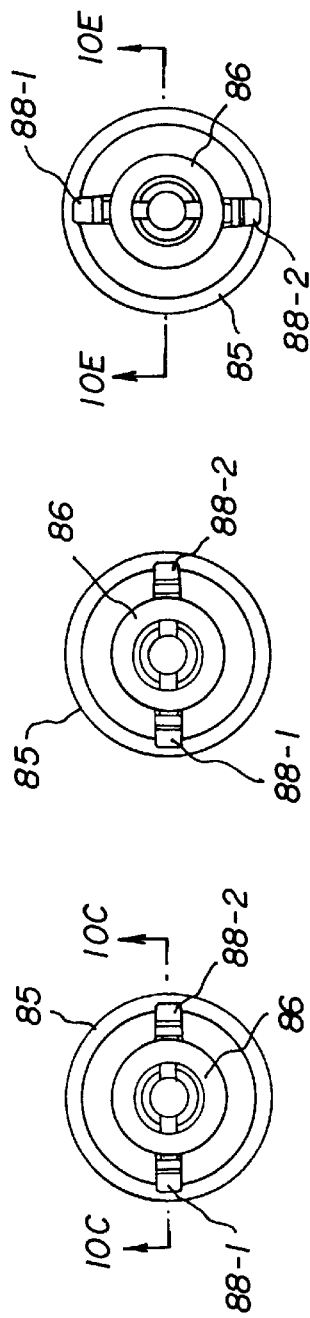
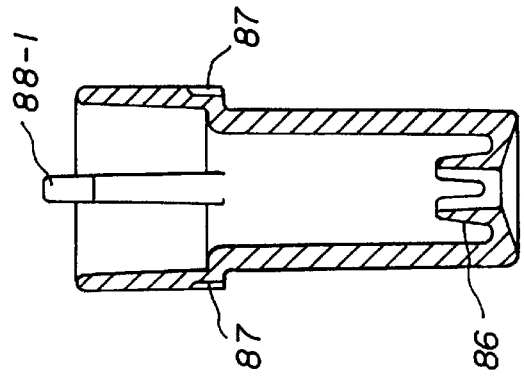
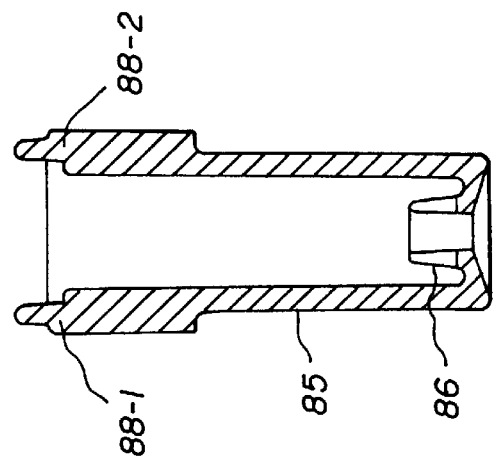
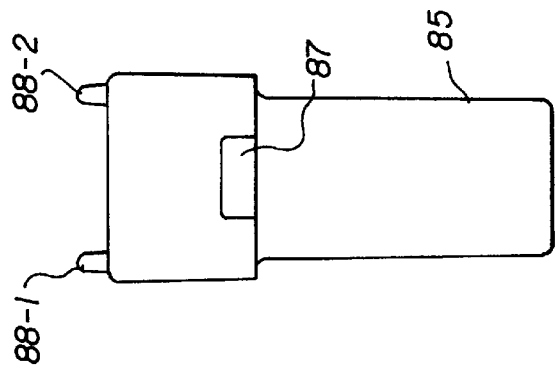

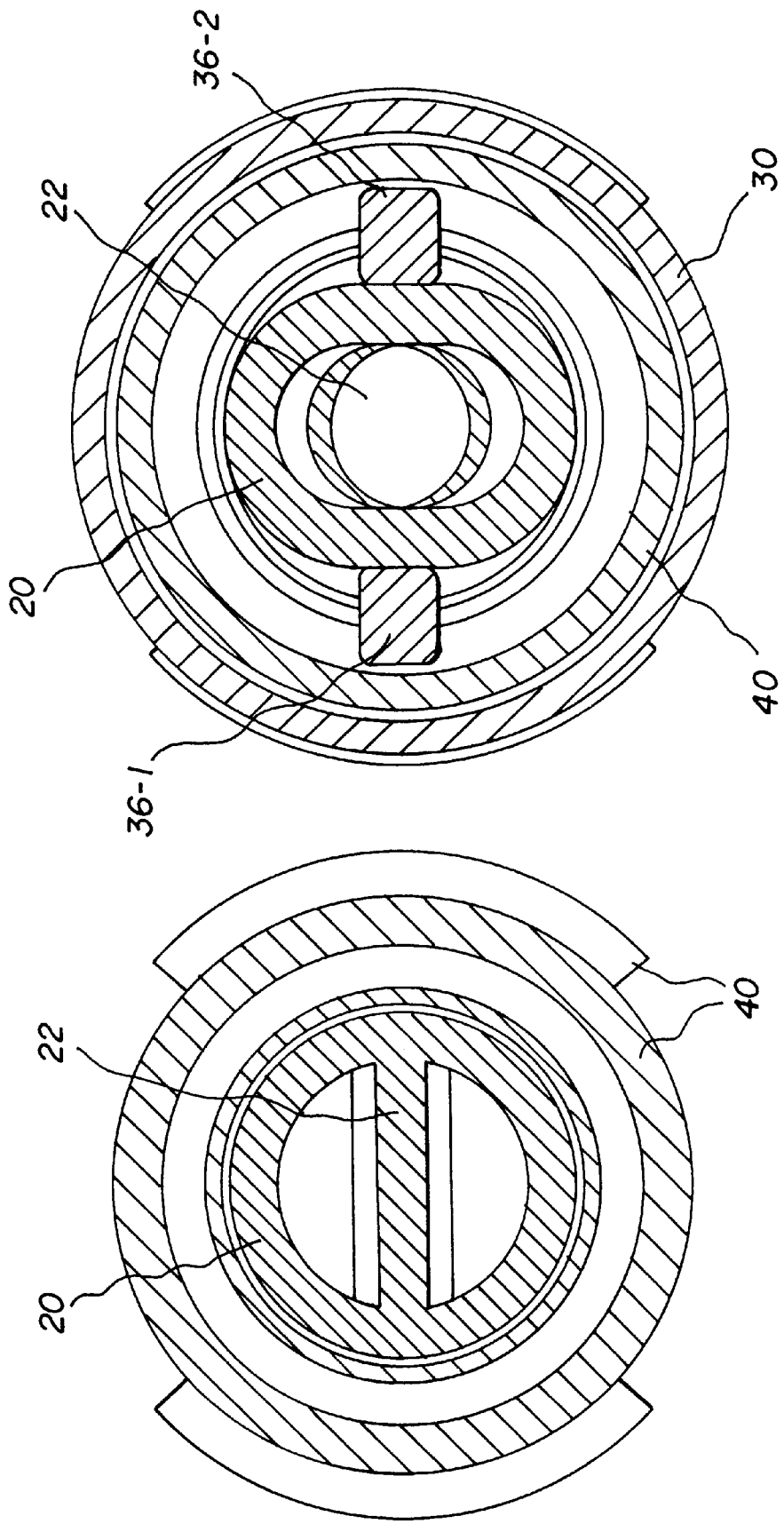

SWABBABLE NEEDLELESS VALVE ADAPTATIONS

BACKGROUND OF THE INVENTION

This invention relates to flow control and, more particularly, to adaptations of Luer activatable and swabbable valves for the needleless control of fluids.

A valve is a device that controls flow, for example, in two directions. Where fluids need to be introduced into, or removed from, the body, it is common practice to do so through a flow control valve connected to a catheter, which is a slender hollow tube inserted into a body passage or cavity for passing fluids. A catheter permits the control of fluid flow both into and out of the body passage.

For example, medication can be injected into a flow control valve that is connected to the catheter. In prior practice, medication from a syringe has been introduced into the control valve using a needle, but this can be undesirable, since needle sticks are to be avoided. A number of attempts have been made to achieve the introduction of medication, or the extraction of fluid, without using syringes with needles.

Illustrative needleless valves are disclosed in Newgard et al., U.S. Pat. No. 5,064,416; Sivert, U.S. Pat. No. 4,915,687; Jackson, U.S. Pat. No. 4,429,856; Kilmarx, U.S. Pat. No. 3,352,531; Faust et al., U.S. Pat. No. 5,116,021 and Lynn, U.S. Pat. No. 5,549,651.

These arrangements typically have the objection that air borne and other pathogens can enter their inlets without being easily sterilized. While attempts have been made to maintain sterility by capping the inlets, the requirement of caps require open passages during connection, and additional complexity and expense. In addition, caps can become dislodged during storage and handling, rending the devices unusable or requiring special sterilization procedures.

Newgard '416 is representative in having a long inlet passage before there is access to a moveable member which is pierceable and controls flow by the extent to which a valving member can be dilated. Sivert, Johnson, Kilmarx and Faust are similarly objectionable.

Moreover, where valves are accessible by Luer fittings, instead of needles, the Luer fitting enters a long inlet passage before making contact with a moveable member that is unseated to permit fluid flow. Because of tolerance considerations, the inlet passage must be wide enough to accommodate the largest diameter Luer fitting. This means that for smaller diameter Luer fittings, within the tolerance specifications, there is a variable gap between the inlet wall of the valve and the Luer fitting being used to access the valve.

In the case of Lynn '651, no tolerance at all is provided, and a plug that is used to seal an input must be compressed in order to achieve operation.

The result typically is a substantially large area for contamination by pathogens that cannot be neutralized by swabbing of the valve, or, as in Lynn the need to compress a press-fit plug.

Accordingly, it is an object of the invention to overcome the problem of pathogen contamination that arises because of the need for valve inlets to accommodate a wide variety of Luer fitting diameters within the tolerance specifications that apply to such fittings.

Another object is to overcome pathogen contamination without requiring a press-fit plug that requires compression.

Still another consideration is desire to operate flow control devices with low "cracking" pressures, i.e. the pressure at which a control member moves away from its seat. For such devices, it is desirable to use relatively thin diaphragms. Unfortunately, thin diaphragms pose problems of stability. The diaphragm may move slightly away from its central position and become lodged against a side wall, causing a problem of leakage.

The catheters used with flow control valves are of various types. One type includes a tubular member for the introduction of fluids into a blood channel, which may be venous or arterial. Another type is a double-walled flexible tube which terminates at its outer end in two separate branches. One branch continues as an outer tube and terminates at its inner end in a inflatable portion.

The other branch continues as an inner tube with a through passage that extends to the inflatable portion of the outer tube. There are various other types of catheters as well.

With all types of catheters, it is desirable to be able to control the through flow of fluid using a suitable valve, which can be used in non-catheter applications as well.

Accordingly, it is another object of the invention to provide a miniature flow control valve which can be used without needles and is swabbable by being easily wiped with disinfectant across its inlet to eliminate contamination and pathogens. A related object is to allow the valve to be readily usable with devices, such as catheters, to control fluid flow while restricting operation by a patient or unauthorized personnel.

Still another object of the invention is to adapt needleless valves for use in branches of fluid feed systems, such as those which have plural sites for the introduction of fluids.

A further object of the invention is to provide a simple and expendable valve, which can be mass produced, readily assembled and provide ease of operation.

In the attempt to produce a swabbable needleless valve disclosed in Lynn U.S. Pat. No. 5,549,651, issued Aug. 21, 1996, a cylindrical piston with a slit extends from the proximal end of a tubular housing. When the cylindrical piston is sized to be tightly received within a cylindrical bore to effectively sealingly wipe the cylindrical side walls, the slit cannot be opened. If the piston is not tightly received, pathogens can enter the space between the cylindrical side walls and the piston.

Accordingly, a still further object of the invention is to overcome the objections presented by swabbable needleless valves of the Lynn type.

SUMMARY OF THE INVENTION

In accomplishing the foregoing and related objects, the invention provides a housing having an outlet; a cap having an inlet and affixed to the housing, with a flexible flange depending from the inlet of the cap to engage and seal a fitting as it enters the inlet.

The housing can contain an interior seat for a flexible plug that extends within the housing to the cap for sealing the inlet at the flexible flange. The plug has a passageway therein extending from an open end to a head with a slit extending therethrough at the inlet.

The housing contains a symmetric channel surrounding the plug to permit unidirectional expansion of the plug, which expands from a circular to an elliptical cross section. The plug can be expanded by the insertion of a Luer fitment into the inlet of the cap to a stop position within the housing.

In accordance with one aspect of the invention, a side branch is connected to said housing beyond the plug, and the housing contains a plurality of stationary and longitudinally extending ribs, which can have different lengths. The seal plug can have a corrugated and flexible section extending from the head, with the corrugations configured to avoid the entrapment of material within the plug during activation by an external fitment inserted into the inlet of a valve containing the plug.

In accordance with another aspect of the invention, the cap is snapped on to a housing to form a swabbable needleless insert member.

In a method of adapting a valve to adapters having various tolerances comprising the steps include: (a) providing a flexible axial wall extending inwardly from an input; and (b) accommodating tolerance variations in actuators inserted into the input by having the flexible axial wall surroundingly engage each inserted actuator, regardless of tolerance variations.

The method can include inwardly leveraging of the flexible axial wall from an internal valve wall surrounding the valve input. A main channel can be provided that extends from the input and a branch channel can be connected to the main channel.

The method of controlling fluid flow can also include the steps of: (a) providing a housing having an outlet opening; (b) positioning a seal plug in the housing; and (c) inserting a cap having an inlet onto the housing with the seal plug extending and sealing the inlet of the cap.

The seal plug can have a slit at the inlet, and the method further include the step of inserting an actuator into the inlet: to depress the seal plug and open the slit. The method also can include the step of forcing the plug against ridges extending longitudinal within the housing and into the cap to open the slit.

The method can include the step of expanding the head of the plug into the interior of the cap, expanding the portion of the plug, beyond the head thereof, into the interior of the housing.

The invention provides a miniature flow control valve with a "universal" Luer adaptation by having, depending from its inlet, a flexible flange that engages and seals the Luer fitting as it enters the inlet, regardless of size, for Luer fittings with the standard range of tolerances for such fittings. The flexible flange functions regardless of the Luer fitting diameter, and thus eliminates the possibility of pathogen contamination from the presence of any gap between the fitting and the interior of the valve before activation.

The invention also provides a housing having a centered at its inlet a seal plug that can be cleansed by swabbing, i.e., wiping, the inlet end before the seal plug is depressed by, for example, the blunt end of a syringe in order to open a slit in the plug and permit passage of fluid from the syringe through a longitudinal channel in the seal plug of the valve.

The seal plug abuts an inwardly facing shoulder of the flexible flange, and is held in its closed position until disengaged from the flange by an external member, such as the hollow blunt end of a syringe, or other male Luer adapter, containing fluid that is to be injected through the valve, for example, into a catheter or other medical, fluid-carrying entity.

In accordance with a further aspect of the invention, the plug extends flush with an input opening, or slightly beyond, so that swabbing is easily accomplished;

In a method of the invention other steps include: sealing an input by a pre-loaded force on a depressible seal plug with an input slit; depressing the seal plug to open the slit and uncover a passageway through the plug connected to an output. As a result, the depression of the seal plug permits flow from the input to the output.

The method of the invention avoids the prior art methods which employ slotted seal members and require internal spikes that are sharp or blunt and are needed to penetrate the slotted seal member, requiring heavy opening forces that result in cutting of the seal member because of the need for seal member expansion within a restricted body volume. After several activations with such devices, the result is the introduction of undesirable contaminant particles in the fluid flow.

The method of the invention avoids the prior art methods in which there is a gap, however small, between a seal member and the channel in which the seal member moves. The presence of such a gap inevitably allows pathogens to enter in the interval between the seal member and the channel wall.

The seal plug of the invention is depressible from a position substantially flush with the entrance to the input. Where the entrance has a prescribed level, the seal plug is depressible from the prescribed level, or from below the prescribed level where is desirable to provide a locator for the instrumentality, such as a syringe, by which the seal plug is depressed.

In a method of manufacturing a swabbable valve the steps include: (a) providing opposed openings including an input opening and an output opening; (b) sealing the input opening to present the entry of pathogens by leaving no interval between the input and the seal. The seal can terminating in a slit which is opened by the depression thereof. The position of the seal at the input permits swabbing before depression to allow fluid flow.

DESCRIPTION OF THE DRAWINGS

Other aspects of the invention will become apparent after considering several illustrative embodiments taken in conjunction with the drawings in which:

FIG. 2A is a sectional view of the embodiment of FIGS. 1A and 1C taken along the lines 2A—2A of FIGS. 1A and 1C;

FIG. 2B is a sectional view of the valve of FIG. 1B taken along the lines 2B—2B of FIG. 1B;

FIG. 2C is a sectional view of the valve of FIG. 1B taken along the lines A—A of FIG. 2A;

FIG. 2D is a sectional view of the valve of FIG. 1B taken along the lines B—B of FIG. 2B;

FIG. 2E is a sectional view of the valve of FIG. 1B taken along the lines C—C of FIG. 2B;

FIG. 2F is a sectional view of the valve of FIG. 1B taken along the lines D—D of FIG. 2B;

FIG. 3A is a sectional view of the valve of FIG. 2A during operation by a Luer actuator;

FIG. 3B is a sectional view of the valve of FIG. 2B during operation by a Luer actuator;

FIG. 3C is a sectional view of the actuated valve of FIG. 1B taken along the lines A—A of FIG. 3A;

FIG. 3D is an end view of the actuated valve of FIG. 1B taken with respect to FIG. 3B;

FIG. 3E is a sectional view of the actuated valve of FIG. 1B taken along the lines B—B of FIG. 3B;

FIG. 3F is a sectional view of the actuated valve of FIG. 1B taken along the lines C—C of FIG. 2B;

FIG. 5A is the sectional view of the valve of FIG. 2A with the valve portion removed;

FIG. 5B is the sectional view of the valve of FIG. 2B with the valve portion removed;

FIG. 5C is an end view of the valve housing of FIG. 5A with the valve portion removed;

FIG. 5D is a partial end view of the valve housing of FIG. 5B with the valve portion removed;

FIG. 6A is a plan view of the swabbable, needleless seal plug in the illustrative embodiment of FIGS. 1A–1C;

FIG. 6B is an end view of the swabbable, needleless seal plug of FIG. 6A showing a perpendicularly-disposed end slit in the depressible seal plug of FIG. 6A;

FIG. 6C is a section view of the swabbable, needleless seal plug of FIG. 6A taken along the lines 6C—6C of FIG. 6B;

FIG. 6D is an end view of the swabbable, needleless seal plug of FIG. 6C;

FIG. 6E is a section view of the swabbable, needleless seal plug of FIG. 6A taken along the lines 6E—6E of FIG. 6F;

FIG. 6F is an end view of the swabbable, needleless seal plug of FIG. 6E;

FIG. 7A is an enlarged, partial sectional view of the seal plug head of FIGS. 2B and 6C;

FIG. 7B is an enlarged, partial sectional view of the seal plug tail of FIGS. 2B and 6C;

FIG. 7C is a full-scale view of the seal plug of FIG. 6A;

FIG. 7D is an end view of FIG. 7C;

FIG. 8A is a plan view of an illustrative swabbable, needleless valve insert embodiment of the invention;

FIG. 8B is an end view of the embodiment of FIG. 8A;

FIG. 8C is a sectional view of the embodiment of FIGS. 8A and 8B taken along the lines 8A—8A of FIG. 8D;

FIG. 8D is an end view of the embodiment of FIG. 8C;

FIG. 8E is a sectional view of the valve of FIG. 8A taken along the lines 8E—8E of FIG. 8F;

FIG. 8F is a sectional view of the valve of FIG. 8E taken along the lines 8B—8B of FIG. 8F;

FIG. 8G is a sectional view of the valve of FIG. 8A taken along the lines 8G—8G of FIG. 8H;

FIG. 8H is a sectional view of the valve of FIG. 8G taken along the lines 8C—8C of FIG. 8G;

FIG. 9A is a plan view of an illustrative swabbable, needleless valve insert embodiment of the invention during operation by a Luer actuator;

FIG. 9B is an end view of the valve insert of FIG. 9A;

FIG. 9C is a sectional view of the valve of FIGS. 9A taken along the lines 9D—9D of FIG. 9A during operation by a Luer actuator;

FIG. 9D is a sectional view of the valve of FIGS. 9C taken along the lines 9F—9F of FIG. 9C during operation by a Luer actuator;

FIG. 9E is a sectional view of the valve of FIGS. 9A taken along ttie lines 9E—9E of FIG. 9C during operation by a Luer actuator;

FIG. 9F is a sectional view of the valve of FIGS. 9E taken along the lines 9G—9G of FIG. 9E during operation by a Luer actuator;

FIG. 10A is a plan view of a body for the illustrative swabbable, needleless valve insert embodiment of FIG. 9A;

FIG. 10B is an end view of the body of FIG. 10A;

FIG. 10C is a sectional view of the body of FIG. 10A with the seal plug removed, taken along the lines 10C–10C of FIG. 10B;

FIG. 10D is an end view of the body of FIG. 10C;

FIG. 10E is a sectional view of FIG. 10A taken along the lines 10E—10E of FIG. 10F;

FIG. 10F is an end view of the body of FIG. 10E;

FIG. 11B is an enlargement of FIG. 2F;

FIG. 11C is an enlargement of FIG. 3F; and

DETAILED DESCRIPTION

Figures 1A, 1B, 1C:
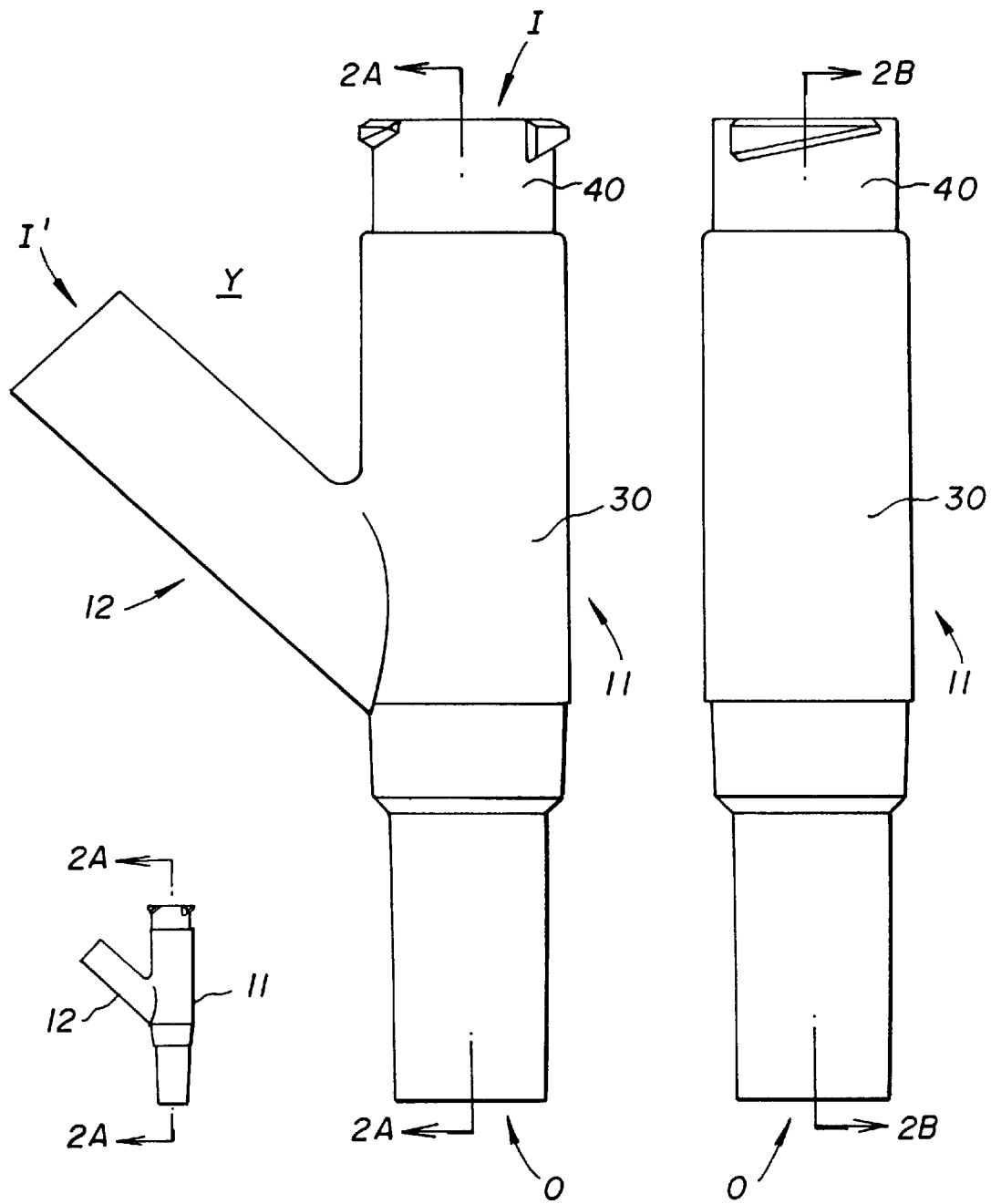
FIG. 1A is a plan view of an illustrative "Y"-site (Wyesite) embodiment of the invention, including a swabbable, needleless valve.
FIG. 1B is a side view of the embodiment of FIG. 1A showing a Luer thread at the inlet end of the swabbable, needleless valve.
FIG. 1C is a full scale view of the embodiment of FIG. 1A.

With reference to the drawings, a "Y"-site embodiment of the invention is provided with a main branch 11 as shown in FIGS. 1A–1C, and a side branch 12 as shown in FIGS. 1A and 1C. The main branch 11 is formed by a housing 30, shown in sectional detail in FIGS. 2A–3B, and a cap 40, shown in detail in FIGS. 4A–4F.

As indicated in FIGS. 2A and 2B, a hollow seal plug 20 extends within the main branch 11 from a seat 31 to a circular flange 41 of the cap 40. The portion of the main branch 11 above the seat 31 to the inlet I of the branch 11 forms a swabbable needleless valve V with the hollow seal plug 20 that is centered in the channel C of the main branch 11 and contains an axial slit 22 that extends to a channel 24 within the seal plug 20.

The housing 30 is illustratively joined and sealed by the ultrasonic cylindrical energy rib 32 at the end 42 of the cap 40, and contains an interior side ridges 36-1 and 36-2 inside cap 40 as shown in FIG. 2B. The channel C of the main branch 11 extends from the seat 31 beyond an opening 33 for the channel C' of the side branch 12 to an outlet O.

As indicated in FIG. 2A, the upper portion or head 21 of the seal plug 20, below the inlet I of the cap 40, slidably engages an internal pendant flange 41 at the upper end of the cap 40, while the intermediate portion 28 of the sealing member 20 surrounds an enlarged region of a channel 24 that extends from the slit 22. The intermediate portion 22 is asymmetrically spaced from the interior wall 34 of the housing 30, which extends to an internal stop 35. The region of the channel 24 below the slit 22 is dome shaped with a diagonal wall that extends to a reduced diameter portion of the channel 24 that connects to the enlarged intermediate.

In addition to its action against the upper portion of the seal plug 20, the circular flexible flange 41 allows the valve V to accommodate a wide variety of male Luer fitments and syringes, as illustrated in conjunction with FIGS. 3A–3B, since the circular flexible flange 41 is biased inwardly towards the bore of the cap 40 and expands outwardly depending upon the diameter of the fitment or syringe that is inserted into the inlet I.

The sealing member 20 is held in its operative sealing position against the circular flange 41 of the cap 40, but other structures may be employed as well. The recess 32 forms a locator for the end 42 of the cap 40 during joining, and is above a Luer prong 36 that extends to the outlet O of the housing 30. Accordingly, the sealing member 20, desirably elastomeric, may be elongated beyond the length indicated before compression.

Extending inwardly from the housing 30 are stationary ridges 36-1 and 36-2 as shown in FIGS. 5A–5D. Also extending inwardly are shorter support ribs 37-1 thru 37-4, also shown in FIGS. 5A–5D. The ridges 36-1 and 36-2 produce flexure of the plug 20 during valve opening. Like the housing 30, the cap 40 can be formed of a moldable plastic, and may be bonded ultrasonically through energy circular rib 32 of the housing 30.

Operation of the valve V is illustrated in FIGS. 3A and 3B using an external member, such as the Luer tip 38 of a syringe. When the valve V is to be operated, the external member is brought into contact with the sealing member 20 at the inlet I. The sealing member 20 is pushed or forced inwardly from its normal seating position encircled by the internal flange 41. When forced inwardly as shown in FIG. 3A, the top of the sealing member 20 is depressed below the internal flange 41 into a region R due to side ridges 36-1 and 36-2, causing the opening of the transverse slit 22 and thus establish open communication for fluid through the central channel 24 of the bore and the outlet O of the housing 30 in either direction, e.g. inwardly or outwardly of the valve V, as indicated by the double-headed arrows A in FIGS. 3A and 3B.

Figure 4A:
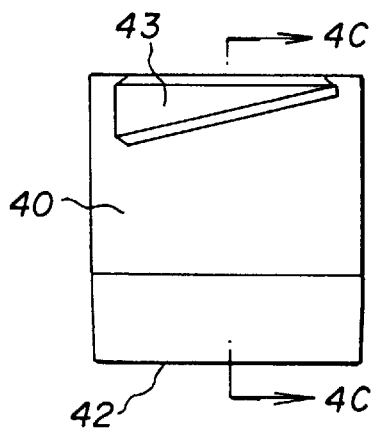
FIG. 4A is a plan view of the cap for the illustrative swabbable, needleless valve insert embodiment of FIG. 1A.
Figure 4B:
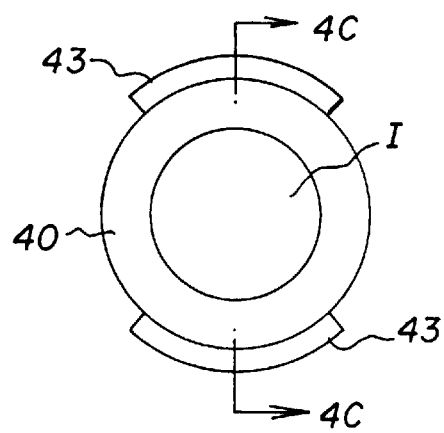
FIG. 4B is an end view of the cap of FIG. 4A.
Figure 4C:
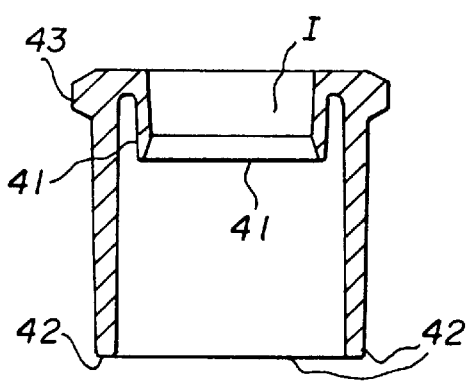
FIG. 4C is a sectional view of the cap of FIG. 4A with the seal plug removed taken along the lines 4C—4C of FIG. 4A and lines 4C—4C of FIG. 4B.
Figure 4D:
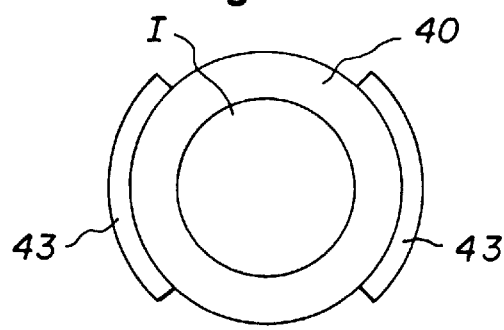
FIG. 4D is an end view of the cap of FIG. 4C before sectioning.
Figure 4E:
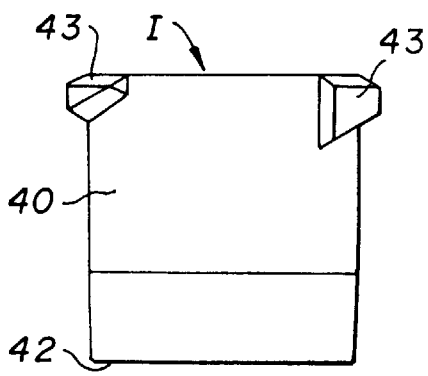
FIG. 4E is a rotated plan view of the cap of FIG. 4A.
Figure 4F:
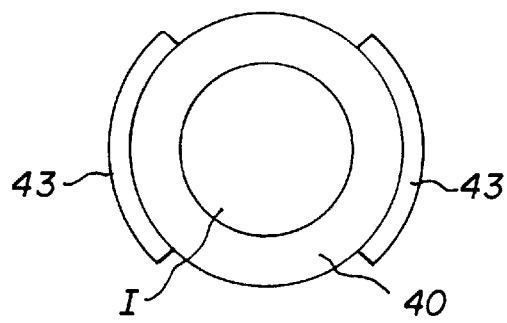
FIG. 4F is an end view of the cap of FIG. 4E.
Figure 4G:
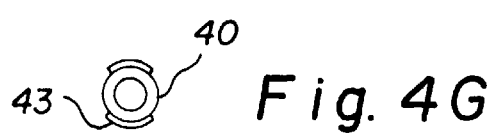
Figure 4H:

Details of the circular flexible flange 41 are shown in the cross section of FIG. 4C which ensures closure of the inlet to prevent any outflow. The flange 41 has walls that diverge away from the inner wall of the associated housing. In addition, the flexibility of the walls for the flange 41 allows the valve V to accommodate a wide variety of Luer fitments and syringes since the inlet I can have a diameter that will receive the largest diameter fitment while the flange 41 assures closure around the smallest diameter fitment below the inlet I. The cap 40 includes partial Luer threads 43.

The valve V of the invention has a wide variety of uses, besides incorporation into a "Y" site of FIGS. 1A–1C where, for example, in an IV (IntraVenous) procedure the side branch 12 of the Y site is connected to a container of solution that is fed through an outlet branch to a patient. The main branch 11 of the site can be used to inject medication into the patient. In prior practice the main branch channel would be accessed through a needle actuated valve, but in the interest of avoiding needle sticks, needleless valves have been substituted. However, as noted above, the typical needleless valve has a long inlet channel in which contaminants and pathogens can accumulate.

When the valves of the invention are used, they are swabbable by being wiped with a disinfectant so that when a Luer fitting is brought into contact with the sealing member 20, the desired medicament can be infused with reduced chance of contamination and no need to used a needle mounted syringe to make the injection.

In a further use of the invention, the plug 20 of the invention is incorporated into an insert member 80, as shown in FIGS. 8A–8F, that also can be used, for example, in an IV (IntraVenous) procedure. In prior practice there would be access through a needle actuated valve, but in the interest of avoiding needle sticks, needleless valves have been substituted. However, as noted above, the typical needleless valve has a long inlet channel in which contaminants and pathogens can accumulate.

With reference to FIG. 8A, the insert member 80 of the invention is provided with a cover cap 81, shown in sectional detail in FIG. 10G–10M, and an insert housing 85, shown in detail in FIGS. 10A–10F.

As indicated in FIGS. 8C and 8E, a seal plug 20 extends within the housing 85 from a seat 86 to a circular flange 82 of the cap 81. The portion of the housing and cap above the seat 86 to the inlet N forms a swabbable needleless valve V' with the annular seal plug 20 that is centered in the cap 32 and contains an axial slot 22 that extends into a channel 24 of the plug 20.

The housing 85 is illustratively joined to the cap 81 by prongs 84-1 and 84-2 at a recess 87. The housing 85 contains extended ribs 88-1 and 88-2. The channel 24 extends to an outlet T.

As indicated in FIG. 8C, the upper portion or head 21 of the seal plug 20, below the inlet N of the cap 81, slidably engages an internal pendant flange 82 at the upper end of the cap 81, while the intermediate portion of the sealing member 20 surrounds an enlarged region of a channel 24 that extends from the slit 22. The intermediate portion is symmetrically spaced from the interior wall of the housing 85. The region of the channel 24 below the slit 22 is dome shaped with a diagonal wall that extends to a reduced diameter portion of the channel 24.

In addition to its action against the upper portion of the seal plug 20, the circular flexible flange 82 allows the valve V' to accommodate a wide variety of male Luer fitments, as illustrated below in conjunction with FIGS. 9C–9E, and syringes since the circular flexible flange 82 is biased inwardly towards the interior of the cap 81 and expands outwardly depending upon the diameter of the fitment or syringe that is inserted into the inlet N.

The sealing member 20 is held in its operative sealing position against the circular flange 82 of the cap 81, but other structures may be employed as well. The sealing member 20 is desirably elastomeric.

Extending inwardly from the housing 85 are stationary ridges 88g-1 and 88E-2 as shown in FIG. 8E to produce flexure of the plug 20. Like the housing 85, the cap 81 can be formed of a moldable plastic. The members 89-1 thru 89-4 become a stop against the internal flange 82. The effect of the moving Luer tip will create a torque that interacts with ribs to maintain alignment.

Operation of the valve V' is illustrated in FIGS. 9A–9F using an external member, such as the Luer tip 89 of a syringe. When the valve V' is to be operated, the external member is brought into contact with the sealing member 20 at the inlet N. The sealing member 20 is pushed or forced inwardly from its normal seating position encircled by the internal flange 82. When forced inwardly as shown in FIG. 9C or 9E, the top of the sealing member 20 is depressed below the internal flange 82 to open the transverse slit 22 and thus establish open communication for fluid through the central channel 24 to the outlet 0 of the housing 85 in either direction, e.g. inwardly or outwardly of the valve V', as indicated by the double-headed arrows A' in FIGS. 9C and 9E.

Figure 10H:
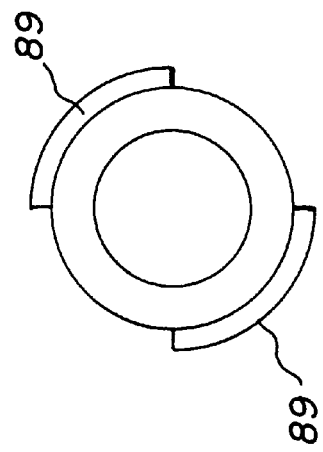
FIG. 10H is an end view of the cap of FIG. 10G.
Figure 10G:
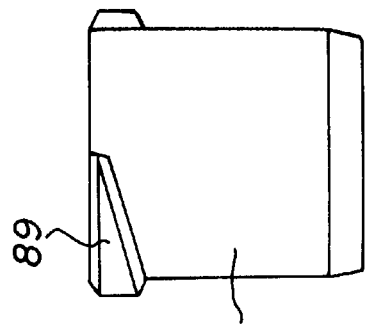
FIG. 10G is a partially rotated plan view of the cap of FIG. 9A.
Figure 10K:
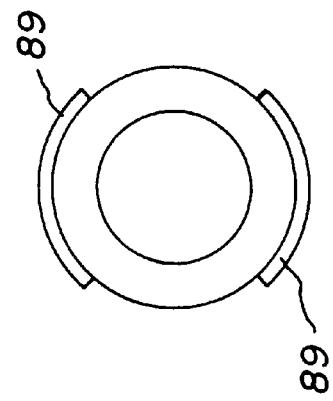
FIG. 10K is an end view of the cap of FIG. 10J.
Figure 10J:
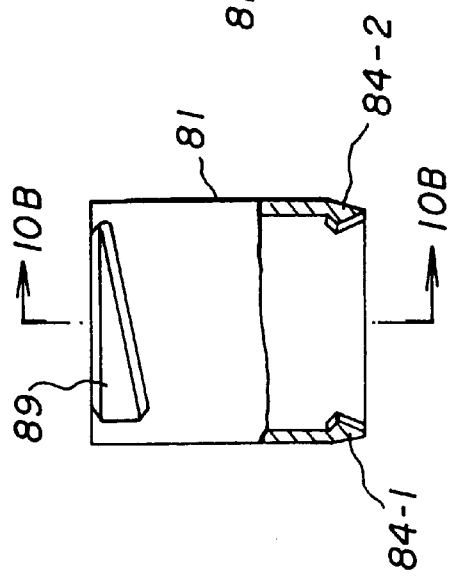
FIG. 10J is a partial sectional view of the cap of FIG. 10G.
Figure 10M:
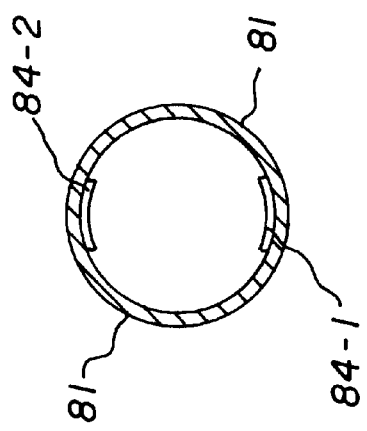
FIG. 10M is a sectional view of the cap of FIG. 10L taken along the lines 10A—10A of FIG. 10L.
Figure 10L:
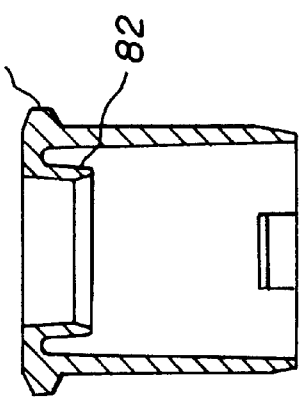
FIG. 10L is a sectional view of the cap of FIG. 10G taken along the lines 10B—10B of FIG. 10J.

Details of the circular flexible flange 82 are shown in the cross section of FIG. 10L which ensures closure of the inlet to prevent any outflow during Luer tip access. In addition, the flexibility of the walls for the flange 82 allows the valve V' to accommodate a wide variety of Luer fitments and syringes since the inlet N can have a diameter that will receive the largest diameter fitment while the flange 82 assures closure around the smallest diameter fitment below the inlet N. The cap 81 includes partial Luer threads 89.

When the valves of the invention are used, they are swabbable by being wiped with a disinfectant so that when a Luer fitting is brought into contact with the sealing member 20, the desired medicament can be infused with reduced chance of contamination and no need to used a needle mounted syringe to make the injection.

Figure 11A:
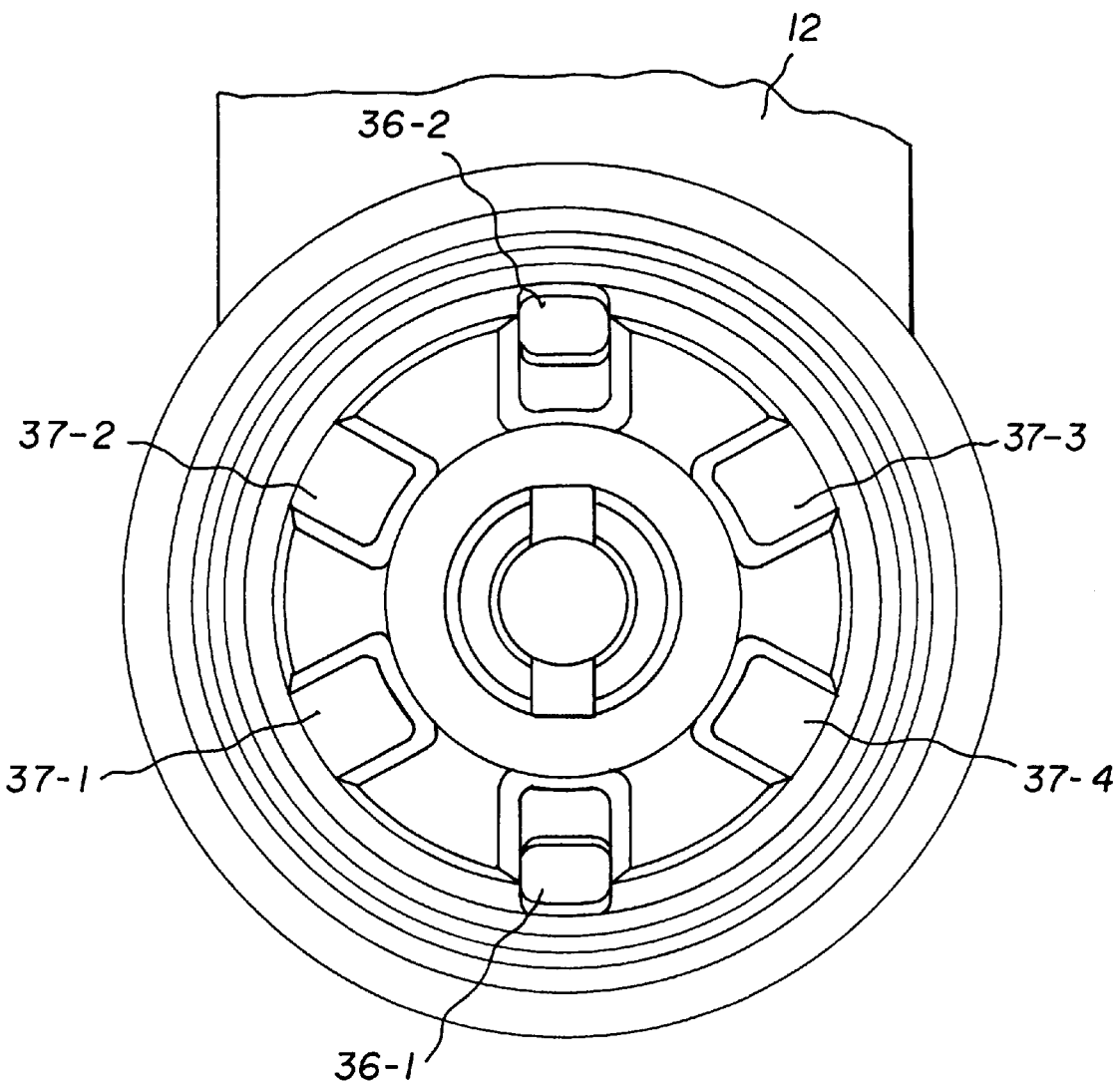
FIG. 11A is an enlargement of FIG. 5C.

FIG. 11 is an enlargement of FIG. 5C showing details of the various components 37-1 through 37-4, 36-1 and 36-2, and 36.

Figure 12:
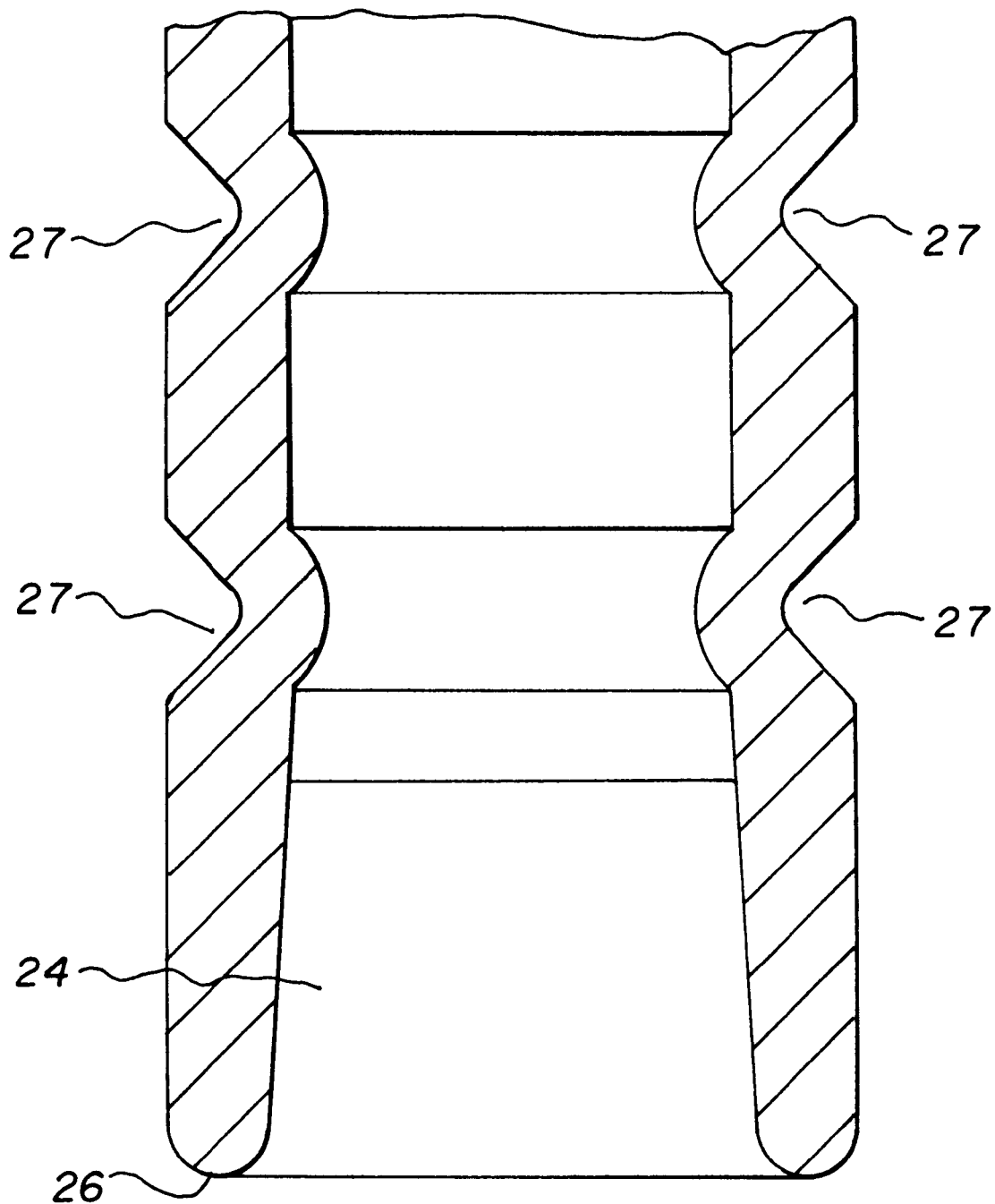
FIG. 12 is an enlargement of FIG. 7B.

FIG. 12 is an enlargement of FIG. 7B showing the structure of the corrugations 27 with an interior wall of the channel 24 that avoids entrapment of material during the operation of Compression and expansion by having no recesses where material otherwise could accumulate.

It is to be noted that the slit 22 shown in the assembly figures is not created until assembly has taken place, which is why the plug 22 of FIGS. 6A through 7D do not show any slit.

While preferred embodiments have been shown and described, it is to be understood that changes in details of construction and method from what has been illustrated may be made without departing from the spirit and scope of the invention as defined by the appended claims.

What is claimed:

1. Apparatus comprising
    a housing having an outlet;
    a cap having an inlet end affixed to said housing and
    a flexible flange depending from said inlet of said cap to engage and circumferentially seal a fitting as it enters said inlet;
    said housing containing an interior seat and a flexible plug that extends against said seat within said housing to said cap for circumferentially sealing said inlet at said flexible flange and a plurality of stationary longitudinally extending ribs.

2. Apparatus as defined in claim 1 wherein said flexible plug has a passageway therein extending from an open end to a head with a slit extending therethrough at said inlet.

3. Apparatus as defined in claim 2 wherein said housing contains a symmetric bore surrounding said flexible plug.

4. Apparatus as defined in claim 3 wherein said symmetric bore permits unidirectional expansion of said flexible plug.

5. Apparatus as defined in claim 4 wherein said flexible plug is expanded by the insertion of a Luer fitment into the inlet of said cap to a stop position within said housing.

6. Apparatus as defined in claim 5 wherein a side branch is connected to said housing beyond said flexible plug.

7. Apparatus as defined in claim 4 wherein said flexible plug expands from a circular to an elliptical cross section.

8. Apparatus as defined in claim 1 wherein said longitudinally extending ribs have different lengths.

9. The method of controlling fluid flow comprising the steps of:
    (a) providing a housing having an outlet opening and a plurality of stationary longitudinally extending ribs,;
    (b) positioning a seal plug in said housing; and
    (c) inserting a cap having an inlet onto said housing with said seal plug extending and sealing the inlet of said cap.

10. The method of claim 9 wherein said seal plug has a slit at said inlet, further including the step of inserting an actuator into said inlet to depress said seal plug and open said slit.

11. The method of adapting a valve to adapters having various tolerances comprising the steps of:
    (a) providing a flexible axial wall extending inwardly from an input of a housing having a plurality of stationary longitudinally extending ribs,; and
    (b) accommodating tolerance variations in actuators inserted into said input by having said flexible axial wall surroundingly engage each inserted actuator, regardless of tolerance variations.

12. The method of claim 11 wherein said flexible axial wall is spaces from and leveraged inwardly from an internal wall surrounding said input.

13. The method as defined in claim 12 including the step of providing a main channel that extends from said input and a branch channel connected to said main channel.

14. Apparatus as defined in claim 13 wherein said flexible plug has a corrugated and flexible section extending from said head.

15. Apparatus comprising
    a housing having an outlet;
    a cap having an inlet and affixed to said housing and
    a flexible flange depending from said inlet of said cap to engage and circumferentially seal a fitting as it enters said inlet;
    wherein said housing contains a plurality of stationary longitudinally extending ribs, an interior seat and a flexible plug that extends against said seat within said housing to said cap for circumferentially sealing said inlet at said flexible flange, and said cap is snapped onto said housing to form a swabbable needleless insert member.

* * * * *